United States Patent [19]

Kim et al.

[11] Patent Number: 5,155,219
[45] Date of Patent: Oct. 13, 1992

[54] PROCESS FOR PRODUCING CYCLODEXTRIN FROM RAW STARCH BY USING ATTRITION MILLING BIOREACTOR

[75] Inventors: Hak S. Kim, Seoul; Yun D. Lee, Kyungki, both of Rep. of Korea

[73] Assignee: Korea Advanced Institute of Science and Techology, Daejeon, Rep. of Korea

[21] Appl. No.: 708,439

[22] Filed: May 30, 1991

[30] Foreign Application Priority Data

Jun. 5, 1990 [KR] Rep. of Korea ............... 8273/1990

[51] Int. Cl.⁵ .................... C08B 37/16; C12P 19/44; C12P 19/04
[52] U.S. Cl. ................... 536/103; 435/74; 435/101
[58] Field of Search .............. 536/103; 435/101, 74

[56] References Cited

U.S. PATENT DOCUMENTS

| | | | |
|---|---|---|---|
| H430 | 2/1988 | Carignan et al. | |
| 4,303,787 | 12/1981 | Horikoshi et al. | 536/103 |
| 4,748,237 | 5/1988 | Rohrbach et al. | 536/103 |
| 4,921,796 | 5/1990 | Rozzell | 536/103 |

*Primary Examiner*—Nathan M. Nutter
*Assistant Examiner*—Jeffrey Culpepor Mullis
*Attorney, Agent, or Firm*—Christie, Parker & Hale

[57] ABSTRACT

A process for producing cyclodextrin from raw starch by mixing a culture supernatant of cyclodextrin gylcosyltransferase-producing microorganism as an enzyme source and a raw starch as a substrate, and stirring the mixture in the presence of an attrition milling media in an attrition milling bioreactor, whereby the reaction is carried out.

7 Claims, 1 Drawing Sheet

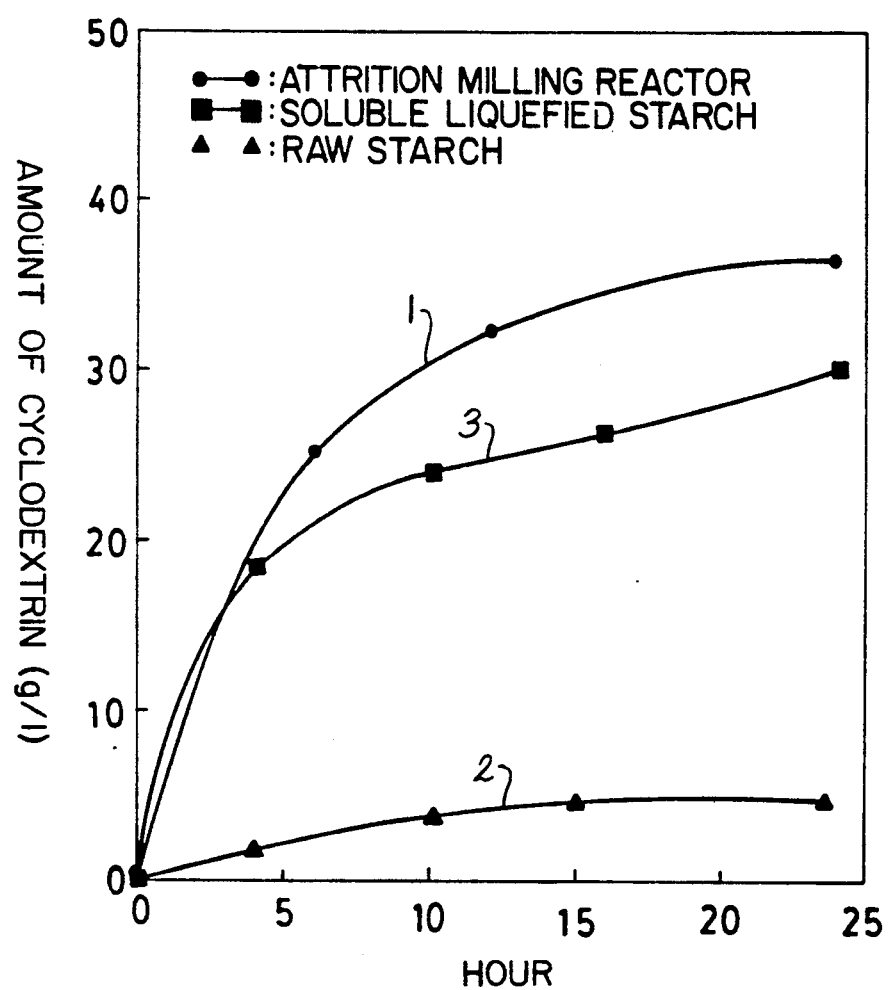

PROCESS FOR PRODUCING CYCLODEXTRIN FROM RAW STARCH BY USING ATTRITION MILLING BIOREACTOR

BACKGROUND OF THE INVENTION

The present invention relates to a process for producing cyclodextrin from raw starch by using an attrition milling bioreactor.

A doughnut-shaped cyclodextrin is a ring-formed nonreductive oligosaccharide in which individual glucose units are linked by $\alpha$-1, 4-glucoside bonds, and there are $\alpha$, $\beta$ and $\gamma$-cyclodextrin consisting of which the number of dextrose molecules are 6,7 and 8, respectively. The sizes and forms of inner cavity of a ring-shaped cyclodextrin are determined by way of the number of dextrose molecule, the inner cavity easily forming an inclusion complex with organic material due to the hydrophobic property. On account of such properties, cyclodextrin has been widely used in fields such as foods, medicines, cosmetics, etc. for stabilizing unstable material, nonvolatilizing volatile material such as aromatics, spices etc, dissolving insoluble material, powdering adhesive material, masking unpleasant odors, promoting emulsification and improving texture, etc.

It is known in the art that cyclodextrin can be industrially prepared by treating starch with cyclodextrin glycosyltransferase after first pretreating the potato starch or corn starch, etc. which is employed as a substrate. In this case the pretreatment requires liquefaction of raw starch by applying heat or adding amylase, which increases the consumption of energy as well as the viscosity of the starch solution and requires multiple unit processes. Thus, the production of cyclodextrin is expensive.

SUMMARY OF THE INVENTION

Therefore, an object of the present invention is to provide a process for preparation of cyclodextrin with high yields by way of an enzymological method in an attrition milling bioreactor, whereby the large consumption of enzyme and energy required for liquefaction can be prevented eliminating the difficulty associated with increased viscosity of the starch solution in liquefaction.

The principle of the present invention is to prepare cyclodextrin with high yields without liquefying the raw starch by changing the structure of the starch by reacting with an enzyme to simplify the enzyme reaction by adding and stirring an attrition milling medium when producing cyclodextrin from raw starch by using cyclodextrin glycosyltransferase which is produced by the bacillus strain.

The process of the present invention employs the culture medium of the microorganism as a direct enzyme source or employs the powdered deposit as a crude enzyme which is obtained by adding organic solvent such as ethanol or methanol to the above culture medium and then freeze-drying.

As for the attrition milling media stainless steel beads, glass beads, ceramic beads and the like were used.

We found that 30 to 50% (v/v) of glass beads of 2-3 mm in diameter may be added to 100 ml of the raw starch solution and then stirred at about 300 to 500 rpm to provide cyclodextrin in high yields against kind, size, amount of addition, agitation speed and the like of the attrition milling media in attrition milling bioreactor.

When 10% of the raw starch is used, about 36.4 g/L of cyclodextrin was produced within 24 hours. Furthermore, $\beta$-amylase or pullulanase can be added to the attrition milling bioreactor, to produce branched cyclodextrin in high yields.

BRIEF DESCRIPTION OF THE DRAWINGS

The accompanying single figure is a graphical representation showing the resulting amounts of cyclodextrin when; 1) produced from raw starch with the addition of an attrition milling medium; 2) produced from raw starch without the addition of any attrition milling media; and 3) produced from liquefied soluble starch.

DETAILED DESCRIPTION OF THE INVENTION

Now this invention will be described in detail in connection with the following examples:

EXAMPLE 1

Microbial culture and a process for producing crude enzyme

Bacillus sp. was cultured at 30° C. in 1% soluble starch medium for 24 hours and the resultant solution was separated by centrifugation to provide a supernatant as a cyclodextrin glycosyltransferase source. This supernatant was employed as a direct enzyme source or was employed as a crude enzyme source, after centrifuging the deposits produced by addition of ethanol or methanol and then freeze-drying and powdering.

EXAMPLE 2

Production of cyclodextrin from raw starch by using crude enzyme in an attrition milling bioreactor In order to research the produced amount of cyclodextrin against the kind and size of an attrition milling medium when cyclodextrin was prepared from raw starch in an attrition milling bioreactor, 10% of the raw starch was added to 0.2M phosphoric buffer solution and then 40 units/ml of the crude enzyme were added. The reaction was carried out at 45° C. At this time, the agitation speed was changed from 100 to 500 rpm and the volume ratio (v/v) for the reaction mixture of the attrition milling media was changed from 10 to 50%. As a result, 30% (v/v) of glass beads of 3 mm in diameter were added and stirred at 300 rpm to provide the highest yield (36.4% yield).

EXAMPLE 3

Production of cyclodextrin from soluble starch 40 units/ml of the crude enzyme obtained in Example 1 were added to a 10% liquefied soluble starch reaction mixture and the reaction was carried out at 45° C. to obtain about 30% yield. The comparative amounts of cyclodextrin produced from 1) raw starch with addition of the attrition milling media or, 2) raw starch without addition of the attrition milling media and 3) liquefied soluble starch are shown in the figure.

EXAMPLE 4

Process for producing cyclodextrin from raw starch by using a supernatant of the culture medium Cyclodextrin was prepared in an attrition milling bioreactor in the same manner as in Example 2 by using the supernatant obtained in Example 1 to provide conversion yield as in Example 2.

EXAMPLE 5

Process for producing cyclodextrin by using fixed enzyme

After cyclodextrin glycosyltransferase was fixed to chitin or chitosan by pretreatment with glutaraldehyde, cyclodextrin was produced by the immobilized cyclodextrin glycosyltransferase in the attrition milling bioreactor to provide a conversion yield as in Example 2. Also, the fixed cyclodextrin glycosyltranferase could be used repeatedly.

EXAMPLE 6

Process for producing branched cyclodextrin

Cyclodextrin was prepared from raw starch in an attrition milling bioreactor, β-amylase or pullulanase, etc. was simultaneously added to provide glucosyl cyclodextrin, a branched cyclodextrin with a conversion yield as in Example 2.

What is claimed is:

1. A process for producing cyclodextrin from raw starch, wherein a culture supernatant of cyclodextrin glycosyltransferase-producing microorganism is used as an enzyme source and the raw starch is reacted by stirring in the presence of attrition milling media in an attrition milling bioreactor.

2. A process according to claim 1, wherein a crude enzyme is employed as the enzyme source which is obtained by adding an organic solvent to the microbial culture supernatant, centrifuging the resulting deposits, and then freeze-drying and powdering the same.

3. A process according to claim 2, wherein said organic solvent is selected from methanol or ethanol.

4. A process according to claim 1, wherein said cyclodextrin glycosyltransferase is fixed to chitin or chitosan by using glutaraldehyde.

5. A process according to any one of claims 1 to 4, wherein said attrition milling media is selected from the group consisting of stainless steel beads, glass beads, ceramic beads, or Teflon beads.

6. A process according to claim 5, wherein the concentration of the raw starch solution is 10%, the agitation speed is 300 rpm and glass beads 3 mm in diameter are used at the attrition milling media.

7. A process according to any one of claims 1, 2 or 4, wherein an enzyme selected from the group consisting of β-amylase and pullulanase is simultaneously added to the enzyme source and reacted with the raw starch in the presence of attrition milling media in an attrition milling bioreactor as a means for producing branched cyclodextrin from raw starch.

* * * * *